United States Patent [19]

Jungblut et al.

[11] Patent Number: 4,977,147
[45] Date of Patent: Dec. 11, 1990

[54] 17-METHYLENE- AND 17-ETHYLIDENE-ESTRATRIENES

[75] Inventors: Peter Jungblut, Neustadt-Bueren; Rudolf Wiechert; Dieter Bittler, both of Berlin, all of Fed. Rep. of Germany

[73] Assignee: Schering Aktiengesellschaft, Berlin, Fed. Rep. of Germany

[21] Appl. No.: 280,803

[22] Filed: Dec. 7, 1988

[30] Foreign Application Priority Data

Dec. 7, 1987 [DE] Fed. Rep. of Germany ....... 3741801

[51] Int. Cl.$^5$ ..................... A61K 31/56; A61K 31/57; A61K 31/58
[52] U.S. Cl. .................................. 514/171; 514/172; 514/176; 514/182
[58] Field of Search ................ 514/172, 182, 171, 176

[56] References Cited

U.S. PATENT DOCUMENTS 3,946,052 3/1976 Crowe et al. ..................... 260/397.5

FOREIGN PATENT DOCUMENTS 46-034421 10/1971 Japan .

OTHER PUBLICATIONS

J. Org. Chem 46, 3326–3328 (1981).

Primary Examiner—Mukund J. Shah
Assistant Examiner—Phil Datlow
Attorney, Agent, or Firm—Millen, White & Zelano

[57] ABSTRACT

A pharmaceutical preparation for treating menopausal symptoms, estrogen deficiency and hormone-dependent tumors, and for use as a contraceptive, comprises a compound of formula I

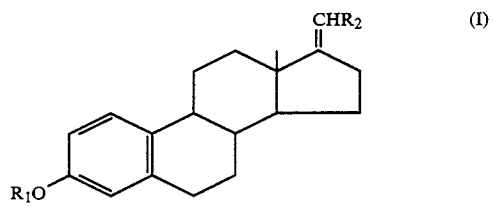

wherein
$R_1$ is hydrogen, methyl, a tetrahydropyranyl group or an acyl group and
$R_2$ is hydrogen or methyl.

23 Claims, No Drawings

17-METHYLENE- AND 17-ETHYLIDENE-ESTRATRIENES

SUMMARY OF THE INVENTION

The invention relates to new pharmaceutical preparations and their use for treatment of menopausal complaints, estrogen deficiency and hormone-dependent tumors and for use as a contraceptive.

The pharmaceutical preparation is characterized by the content of one or more compounds of formula I

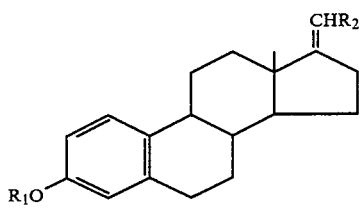

wherein
$R_1$ is hydrogen, methyl, a tetrahydropyranyl group or an acyl group and
$R_2$ is hydrogen or methyl.

Suitable acyl groups are physiologically compatible groups derived from acids customarily used for the esterification of hydroxy steroids. The identity and structure of the acyl moiety are not critical. Suitable acyl groups include organic carboxylic acids of 1–12 carbon atoms, e.g., hydrocarbon acids, pertaining to the aliphatic, cycloaliphatic, aromatic or aromatic-aliphatic series which can be saturated or unsaturated, mono- or poly-basic and/or substituted. Examples that can be mentioned for the substituents are alkyl (e.g., of 1–4 C atoms), hydroxy, alkoxy (e.g., of 1–4 C atoms), oxo or amino groups (e.g., amino and mono- or dialkylamino (1–4 C-alkyl groups)) and halogen atoms. Among these are also the usual inorganic acids.

Examples of such carboxylic acids of 1–12 carbon atoms include alkanoyl groups from formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, trimethylacetic acid, tertbutylacetic acid, cyclopentylacetic acid, diethylaminoacetic acid, lactic acid, succinic acid, adipic acid; other preferred groups include benzoic acid, nicotinic acid, morpholinoacetic acid, etc.

Examples of inorganic acids include sulfuric and phosphoric acids.

The esters of succinic acid, adipic acid, sulfuric acid, and phosphoric acid can optionally be converted with an alkali into the water-soluble salts.

Hetero acyl groups can be derived from heterocyclic acids comprising 1–2 fused rings, wherein each ring contains 4–7 ring atoms and 1–2 hetero atoms, the hetero atoms comprising O, N and/or S. Suitable acyl groups include that from pyrrolidino-, piperidino-, piperazino-, morpholinosulfonic acid, etc.

Suitable halogen atoms throughout the foregoing are fluorine, chlorine, bromine and iodine, preferably fluorine and chlorine.

The compounds of formula I with $R_1$ meaning hydrogen atom or acetyl are already known.

17-methylene-1,3,5(10)-estratrien-3-ol and the 3-acetate are described, for example, in J. Org. Chem. 1981, 46, 3326–3328, as intermediate products for production of D-homosteroids. 17-ethylidene-1,3,5(10)-estratrien-3-ol is an intermediate product for production of the corresponding 17-beta ethyl compound (U.S. Pat. No. 3,946,052). It is reported of 17-methylene compounds (and specifically 3-OH, 3-ethoxy, 3-benzoyloxy, 3-(2'-tetrahydropyranyloxy) and 3-methoxy 17-methylene estratriene) in Jap. Patent No. 71034421 (Chem. Abstracts Vol. 75 (1971) 151978z) that they are anticholesterol agents. The patent also reports that these compounds have a significantly diminished estrogenic effect. The entire contents of this patent is hereby incorporated by reference.

It has been found that the estratrienes substituted in the 17-position by methylene or ethylidene are clearly different from estrones. In comparison with the estrones, from which they are produced, the compounds of formula I show a lower affinity to the estrogen receptors than estradiol, but as compared with estradiol, surprisingly bring about increased cellular membrane and blood/lymphatic vessel permeability.

In the estrogen receptor binding test for estrogenic activity with the use of cytosol from pig uterus homogenate and of 6,7³H estradiol as the reference compound, the compounds of formula I show a lower affinity for the estrogen receptor.

The following table indicates the competition at the receptor in percent.

TABLE

| Estrogen Receptor Binding Test | | |
|---|---|---|
| Compound | Mol | % Competition |
| Estradiol | $2 \times 10^{-8}$ | 49 |
| | $2 \times 10^{-7}$ | 88 |
| | $2 \times 10^{-6}$ | 96 |
| 17-methylene-1,3,5(10)-estratrien-3-ol | $2 \times 10^{-8}$ | 8 |
| | $2 \times 10^{-7}$ | 25 |
| | $2 \times 10^{-6}$ | 73 |
| 17-ethylidene-1,3,5(10)-estratrien-3-ol | $2 \times 10^{-8}$ | 5 |
| | $2 \times 10^{-7}$ | 11 |
| | $2 \times 10^{-6}$ | 48 |

In the uterus growth test with immature, 23-day-old Sprague-Dawley rats, for example, 17-methylene-1,3,5(10)-estratrien-3-ol exhibits only 1/70 of the uterotropic activity of estradiol. The value of 1/70 of the estradiol is found both if it is based on the uterus wet weights including the intrauterine liquid, and if the DNA content is taken as measurement of the uterus cell content.

For performing the test, the immature female rats receive estradiol or 17-methylene-1,3,5(10)-estratrien-3-ol subcutaneously once a day for 3 days. On the 4th day, the animals are sacrificed and the uterus weight or DNA content per uterus is determined.

A uterus weight of 50 mg or a DNA content of 302 micrograms is obtained with 0.07 microgram of estradiol or with 5 micrograms of 17-methylene-1,3,5(10)-estratrien-3-ol.

Upon local administration of estradiol or 17-methylene-1,3,5(10)-estratrien-3-ol into the uterine lumen of a female pig, a uterine edema is produced, the onset of which, using the 17-methylene compound, begins about 30 minutes later than with the estradiol but occurs to the same extent as with estradiol. The extent of the edema can be determined by ascertaining the albumin and DNA content of the uterus.

Intrauterine injection of $1 \times 10^{-6}$-molar solutions (20–50 ml/uterus) of the compounds to be tested was performed. With estradiol, an increase of the albumin content to about 17 mg of albumin/1 mg of DNA resulted after 120 minutes. With the corresponding 17-methylene compound, an increase to the same value resulted after 150 minutes.

Introduction of the test compound into a uterine horn of a female pig brings about edema formation only at that location; the untreated horn is not affected.

Accordingly, the finding for the compounds of formula I is an activity disproportionation indicating a lower activity in the cell nucleus (e.g., less transcription and/or translation) mediated by the estrogen receptor, with an edema formation that is unchanged as compared with estradiol. Thus, the compounds of this invention are surprisingly useful estrogenic compounds despite their low affinity for the estrogen receptor, and contrary to the teachings of JP No. 71034421 for its compounds, due to this unexpected disproportionation of activity effects.

The compounds of formula I are substrates for intracellular enzymes, the products of which lead to an increase in cellular membrane and blood/lymphatic vessel permeability and thus edema, which can be demonstrated as so-called "water imbibition" in the form of a massive edema in the target organ, the uterus. These compounds are especially suitable for the treatment of climacteric complaints, as well as generally for the treatment of symptoms occurring due to defunctionalization of the second activity segment of estradiol, e.g., osteoporosis, amenorrhea, troublesome side effects of monthly withdrawal bleeding, atrophic vaginitis, etc.

The active compounds are preferably administered orally, e.g. to mammals including humans, but they can also be administered locally and parenterally. For this purpose, the active compounds are processed according to conventional methods for the customary forms of administration together with the additives, excipients and/or solubilizers customary in galenic pharmacy. For the preferred oral administration, especially suitable are tablets, dragees, capsules, pills, aqueous suspensions or alcoholic solutions, and for local and parenteral administration, especially ointments and, respectively, oily solutions, such as, for example, sesame oil or castor oil solutions which can additionally contain, if desired, a solubilizer, e.g., benzyl benzoate.

The concentration of active compound in the pharmaceutical preparations depends on the type of administration and the field of usage. Thus, for example, tablets, dragees, capsules or pills can contain 50-200 μg of active compound per dosage unit, and oily solutions or ointments can contain 1-20 μg of active compound per milliliter.

In a preferred embodiment, the oral form of administration contains 50-150 μg of active agent.

After treating therapeutically castrated women, as well as menopausal women, all of whom suffered from hot flashes and moodiness, with a daily dosage of 50-150 μg of active compound according to formula I, a marked decrease in discomfort occurred as early as after 2 days.

The systemic administration of compounds of formula I to Sprague-Dawley rats with mammary tumors induced by 7,12-dimethylbenzanthracene leads to cessation of tumor growth without any marked effect on the estrous cycle. The compounds are thus likewise suitable for the treatment of hormone-dependent tumors analogously to the known compound Tamoxifen. With the use of the compounds in amounts of 0.15-15 μg per kg, stimulation of growth of existing hormone-dependent tumors is prevented.

This antitumor activity can be demonstrated using any conventional protocol, e.g., as described in Science 137 (1962), 257-262.

The compounds of formula I, being substances with a selective estrogenic activity, can also be utilized in preparations for contraception, preferably in combination with a progestationally active hormone component, e.g., levonorgestrel, gestodene, or desogestrel. Forms of administration that can be given orally contain preferably 50-200 μg of a compound of formula I and 50-500 μg of a strongly effective gestagen per day. The compounds are administered analogously to the known compound Microgynon ®.

The compounds of formula I are either known or can be produced from known 3-hydroxy compounds according to methods known in the art by esterification or etherification.

The esterification (acylation) preferably takes place with pyridine/acid anhydride or pyridine/acid chloride at room temperature.

Alkylating compounds, such as diazoalkanes or dialkylsulfates, can be used for the etherification.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application, West German No. P 37 41 801.7, filed Dec. 7, 1987, are hereby incorporated by reference.

EXAMPLES

Directions for Production of compounds of general Formula I (1) 17-Methylene-1,3,5(10)-estratrien-3-ol 74.6 ml of 15% butyllithium solution in hexane is instilled into a suspension of 44.0 g of methyltriphenylphosphonium bromide in 200 ml of dioxane under an argon stream and ice-bath cooling. It is then stirred for 1.5 hours more at room temperature. Then 6.0 g of 3-(tetrahydropyran-2'-yloxy)- 1,3,5(10)-estratrien-17-one is added, the hexane is distilled off up to boiling point of 100° C. and then the reaction mixture is refluxed for 19 hours. After ice water precipitation the substance is extracted with dichloromethane. After drying and concentration by evaporation the residue is chromatographed on silica gel, and 6.1 g of 17-methylene-3-(tetrahydropyran-2'-yloxy)-1,3,5(10)-estratriene with a melting point of 73.5 ° C. is obtained.

6 ml of 8% by volume of sulfuric acid is added to a solution of 6.0 g of 17-methylene-3-(tetrahydropyran-2'-yloxy)-1,3,5(10)-estratriene in 60 ml of methanol and is allowed to stand for 4 hours at room temperature. Then reaction solution is then diluted with ether, washed with water, dried and concentrated by evaporation. The residue is recrystallized from hexane and 4.1 g of 17-methylene-1,3,5(10)-estratrien-3-ol with a melting point of 133.5° C. is obtained.

(2) 3-Methoxy-17-methylene-1,3,5(10)-estratriene 200 mg of 17-methylene-1,3,5(10)-estratrien-3-ol is dissolved in 115 ml of 0.5 molar sodium hydroxide solution, is mixed with 2.5 ml of dimethyl sulfate and stirred overnight at room temperature. The reaction solution is extracted with dichloromethane, the organic phase is washed with water, dried and concentrated by evaporation. The residue is chromatographed on silica gel, and 170 mg of 3-methoxy-17-methylene-1,3,5(10)-estratriene is obtained.

(3) 3-Acetoxy-17-methylene-1,3,5(10)-estratriene 200 mg of 17-methylene-1,3,5(10)-estratrien-3-ol in 1 ml of pyridine and 0.5 ml of acetic anhydride is allowed to stand overnight at room temperature. It is then diluted with ice water, the precipitated precipitate is filtered off, taken up in dichloromethane, dried and concentrated by evaporation. The residue is chromatographed on silica gel, and 185 mg of 3-acetoxy 17-methylene-1,3,5(10)-estratriene is obtained.

(4) 3-Butyryloxy-17-methylene-1,3,5(10)-estratriene 250 mg of 17-methylene-1,3,5(10)-estratrien-3-ol is reacted in 1.5 ml of pyridine with 0.75 ml of butyric acid anhydride and worked up as described in example 3. After chromatography on silica gel, 245 mg of 3-butyryloxy-17-methylene-1,3,5(10)-estratriene is obtained.

(5) 17-Ethylidene-1,3,5(10)-estratrien-3-ol 3.22 g of potassium tert-butylate in added by portions to a suspension of 10.6 g of ethyltriphenylphoshonium bromide in 50 ml of dimethyl sulfoxide and stirred for 1 more hour at room temperature. Then a solution of 4.0 g of tert-butyl-dimethylsilyloxy-1,3,5(10)-estratrien-17-one in 50 ml of dimethyl sulfoxide is instilled and stirred for 3 more hours at room temperature. The reaction solution is diluted with ether, washed with water, dried and concentrated by evaporation. The residue is chromatographed on silica gel, and 450 mg of (syn) 17-ethylidene-1,3,5(10)-estratrien-3-ol is obtained.

(6) 17-Ethylidene-1,3,5(10)-estratriene-3-methyl ether 100 mg of (syn) 17-ethylidene-1,3,5(10)-estratrien-3-one in 57.5 ml of 0.5 molar sodium hydroxide solution is reacted with 1.25 ml of dimethyl sulfate and worked up as described in example 2. After chromatography on silica gel, 75 mg of (syn) 17-ethylidene-1,3,5(10)-estratriene-3-methyl ether is obtained.

(7) 17-Ethylidene-3-propionyloxy-1,3,5(10)-estratriene 100 mg of (syn) 17-ethylidene-1,3,5(10)-estratrien-3-ol in 1 ml of pyridine is reacted with 0.5 ml of propionic acid anhydride and worked up as described in example 3. After chromatography on silica gel, 95 mg of (syn) 17-ethylidene-=3-propionyloxy-1,3,5(10)-estratriene is obtained.

EXAMPLE 1

Composition of a dragee

| Example 1 Composition of a dragee | |
|---|---|
| 0.050 mg | 17-methylene-1,3,5(10)-estratrien-3-ol |
| 46.450 mg | Lactose |
| 26.800 mg | Corn starch |
| 3.000 mg | Poly(1-vinyl-2-pyrrolidone) average MW 25,000 |
| 3.700 mg | Talc |
| 80.000 mg | Total weight, supplemented to about 140 mg with the usual sugar mixture |

EXAMPLE 2

Composition of an alcoholic solution 1 mg of 17-methylene-1,3,5(10)-estratrien-3-ol is dissolved in 10 ml of 46% ethyl alcohol.

Ten drops (0.5 ml) contain 50 μg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A composition comprising a compound of formula I

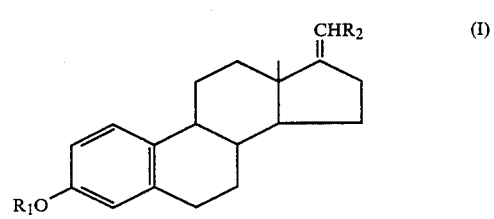

wherein $R_1$ is methyl, tetrahydropyranyl or the acyl group of a $C_{1-12}$ hydrocarbon carboxylic acid or a heterocyclic acid having 1-2 fused rings, wherein each ring contains 4-7 ring atoms and 1-2 hetero contains 4-7 ring aotms and 1-2 hetero atoms which are O, N and/or S, said acyl groups being optionally substituted by $C_{1-4}$ alkyl, hydroxy, $C_{4-4}$-alkoxy, oxo, amino or halogen, or of a mineral acid, and $R_2$ is methyl, and a pharmaceutically acceptable excipient.

2. A composition comprising a compound of formula I

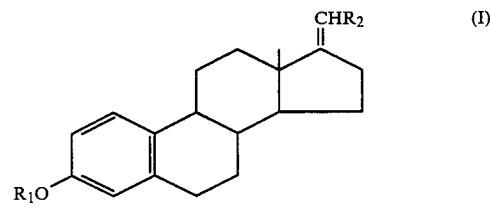

wherein $R_1$ is the acyl group of a $C_{1-12}$ hydrocarbon carboxylic acid or a heterocyclic acid having 1-2 fused rings, wherein each ring contains 4-7 ring atoms and 1-2 hetero atoms which are O, N and/or S, said acyl groups being optionally substituted by C₁₋₄ alkyl, hydroxy, C₄₋-alkoxy, oxo, amino or halogen, or of a mineral acid, and R₂ is hydrogen, and a pharmaceutically acceptable excipient.

3. A composition of claim 1, wherein R₁ is alkanoyl.

4. A composition of claim ', wherein R₁ is alkanoyl.

5. A composition of claim 1, wherein the amount of said compound is 50–200 μg.

6. A composition of claim 2, wherein the amount of said compound is 50–200 μg.

7. A method of treating menopausal symptoms, comprising administering a composition comprising a compound of formula I

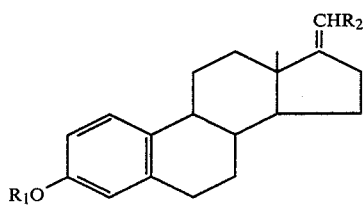

wherein

R₁ is hydrogen, methyl, tetrahydropyranyl or the acyl group of a C₁₋₁₂ hydrocarbon carboxylic acid or a heterocyclic acid having 1–2 fused rings, wherein each ring contains 4–7 ring atoms and 1–2 hetero atoms which are O, N and/or S, said acyl groups being optionally substituted by C₁₋₄ alkyl, hydroxy, C₁₋₄-alkoxy, oxo, amino or halogen, or of a mineral acid, and R₂ is hydrogen or methyl, and a pharmaceutically acceptable excipient.

8. A method of treating estrogen deficiency, comprising administering a composition comprising a compound of formula I

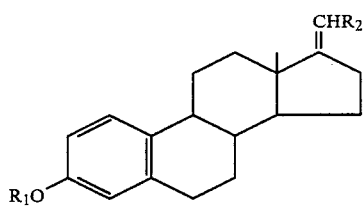

wherein

R₁ is hydrogen, methyl, tetrahydropyranyl or the acyl group of a C₁₋₁₂ hydrocarbon carboxylic acid or a heterocyclic acid having 1–2 fused rings, wherein each ring contains 4–7 ring atoms and 1–2 hetero atoms which are 0, N and/or S, said acyl groups being optionally substituted by C₁₋₄ alkyl, hydroxy, C₁₋₄-alkoxy, oxo, amino or halogen, or of a mineral acid, and R₂ is hydrogen or méthyl, and a pharmaceutically acceptable excipient.

9. A method of treating hormone-dependent tumors, comprising administering a composition comprising a compound of formula I

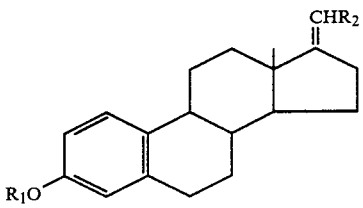

wherein

R₁ is hydrogen, methyl, tetrahydropyranyl or the acyl group of a C₁₋₁₂ hydrocarbon carboxylic acid or a heterocyclic acid having 1–2 fused rings, wherein each ring contains 4–7 ring atoms and 1–2 hetero atoms which are O, N and/or S, said acyl groups being optionally substituted by C₁₋₄ alkyl, hydroxy, C₁₋₄-alkoxy, oxo, amino or halogen, or of a mineral acid, and R₂ is hydrogen or methyl, and a pharmaceutically acceptable excipient.

10. A method of preventing pregnancy, comprising administering to a female mammal a composition a compound of formula I

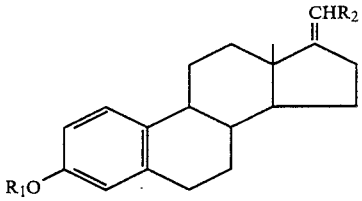

wherein

R₁ is hydrogen, methyl, tetrahydropyranyl or the acyl group of a C₁₋₁₂ hydrocarbon carboxylic acid or a heterocyclic acid having 1–2 fused rings, wherein each ring contains 4–7 ring atoms and 1–2 hetero atoms which are O, N and/or S, said acyl groups being optionally substituted by C₁₋₄ alkyl, hydroxy, C₁₋₄-alkoxy, oxo, amino or halogen, or of a mineral acid, and R₂ is hydrogen or methyl, and a pharmaceutically acceptable excipient.

11. A method of preventing pregnancy, comprising administering to a female mammal, in combination, a composition, comprising a compound of formula I

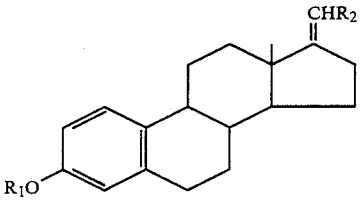

wherein

R₁ is hydrogen, methyl, tetrahydropyranyl or the acyl group of a C₁₋₁₂ hydrocarbon carboxylic acid or a heterocyclic acid having 1–2 fused rings, wherein each ring contains 4–7 ring atoms and 1–2 hetero atoms which are O, N and/or S, said acyl groups being optionally substituted by C₁₋₄ alkyl, hydroxy, C₁₋₄-alkoxy, oxo, amino or halogen, or of a mineral acid, and R₂ is hydrogen or methyl, a progestationally active compound and a pharmaceutically acceptable excipient.

12. A method of treating menopausal symptoms comprising administering a composition of claim 1.

13. A method of treating menopausal symptoms, comprising administering a composition of claim 2.

14. A method of treating estrogen deficiency, comprising administering a composition of claim 1.

15. A method of treating estrogen.. deficiency, comprising administering a composition of claim 2.

16. A method of treating hormone-dependent tumors, comprising administering a composition of claim 1.

17. A method of treating hormone-dependent tumors, comprising administering a composition of claim 2.

18. A method of preventing pregnancy, comprising administering to a female mammal a composition of claim 1.

19. A method of preventing pregnancy, comprising administering to a female mammal a composition of claim 2.

20. A method of preventing pregnancy, comprising administering to a female mammal, in combination, a composition of claim 1 and a progestationally active compound.

21. A method of preventing pregnancy, comprising administering to a female mammal, in combination, a composition of claim 2 and a progestationally active compound 22. A composition of claim 1, wherein the compound is 17-ethylidene-1,3,5(10)-estratriene methyl ether or 17-ethylidene-3-propionyloxy-1,3,5(10)-estratriene.

23. A composition of claim 2, wherein the compound is 3-acetoxy-17-methylene-1,3,5(10)-estratriene or 3-butyryloxy-17-methylene-1,3,5(10)-estratriene.

* * * * *

UNITED STATES PATENT AND TRADEMARK OFFICE
CERTIFICATE OF CORRECTION

PATENT NO. : 4,977,147
DATED : December 11, 1990
INVENTOR(S) : Peter JUNGBLUT et al.

It is certified that error appears in the above-identified patent and that said Letters Patent is hereby corrected as shown below:

Column 8

Claim 10; Line 2:

Please insert "comprising" after composition.

Signed and Sealed this

Eighth Day of June, 1993

Attest:

MICHAEL K. KIRK

*Attesting Officer*  *Acting Commissioner of Patents and Trademarks*